United States Patent
Giebeler

[11] Patent Number: 6,165,146
[45] Date of Patent: Dec. 26, 2000

[54] CERVICAL BRACE

[76] Inventor: Wolfgang Giebeler, Eisenbachweg 16, D-61267 Neu-Anspach, Germany

[21] Appl. No.: 09/214,087
[22] PCT Filed: Apr. 29, 1998
[86] PCT No.: PCT/EP98/02521
§ 371 Date: Dec. 28, 1998
§ 102(e) Date: Dec. 28, 1998
[87] PCT Pub. No.: WO98/49928
PCT Pub. Date: Nov. 12, 1998

[30] Foreign Application Priority Data

May 2, 1997 [DE] Germany .................. 197 18 674

[51] Int. Cl.[7] ....................................... A61F 5/00
[52] U.S. Cl. .............................................. 602/18
[58] Field of Search ................. 602/18; 128/DIG. 23

[56] References Cited

U.S. PATENT DOCUMENTS

| | | | |
|---|---|---|---|
| 3,024,784 | 3/1962 | Monfardini | 602/18 |
| 3,189,026 | 6/1965 | Barnett | 602/18 |
| 3,364,926 | 1/1968 | Alderson | 602/18 |
| 4,958,631 | 9/1990 | Sarkozi | 602/87 |
| 5,211,623 | 5/1993 | Sarkozi | 602/18 |

FOREIGN PATENT DOCUMENTS 33 18 938 A1  5/1983  Germany .

Primary Examiner—Kim M. Lewis
Attorney, Agent, or Firm—Heslin & Rothenberg, P.C.

[57] ABSTRACT

A cervical brace includes a brace body which can be placed around the neck of a patient and fastened and unfastened at the narrow ends. Upper and lower rims of the brace body are adapted to fit the anatomy of the head and shoulder area around the neck respectively. The brace body includes upper and lower sections divided by a weakened zone or attenuation area. The brace body exhibits, at least over a portion of its length, a tapering curvature to its lower rim, so that the lower segment, upon application of the cervical brace, fits tightly around the entire base of the neck of the wearer.

11 Claims, 4 Drawing Sheets

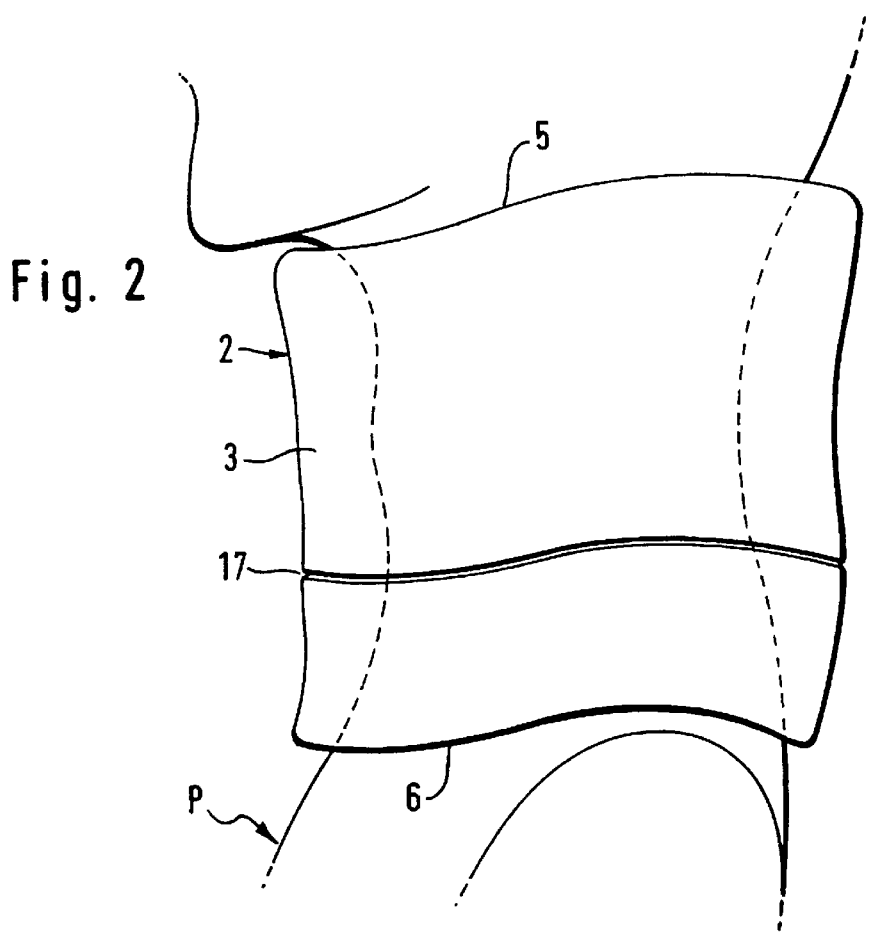
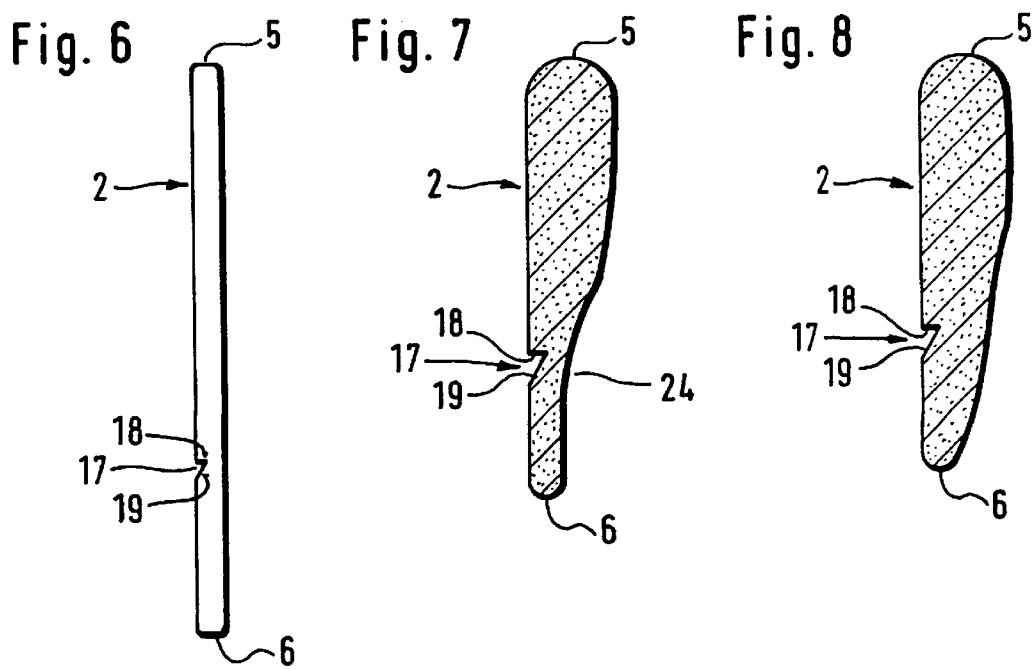

CERVICAL BRACE

BACKGROUND OF THE INVENTION

The invention concerns a cervical brace.

A cervical brace which can be placed about the neck of a patient has been made common knowledge by EP 0 385 114 B 1. The cervical brace of that patent has proved itself in practice. A disadvantage thereof, is that this cervical brace can slide on the neck of the patient.

A cervical brace, which is within the generic concepts of claim 1 is known from U.S. Pat. No. 5,211,623. This known cervical brace exhibits a brace element, with is comprised of two roll shaped segments, which are arranged in a hose-like element, one above the another. The roll shaped segments are filled with soft material. The disadvantage is, that the lower segment does not closely fit the neck contact piece, whereby in this area only a small restriction of movement freedom is assured.

BRIEF SUMMARY OF THE INVENTION

Thus, the present invention has the purpose of creating a cervical brace with increased limitation of motion and at the same time possessing a high degree of comfort in wearing, and in which cervical brace there is no danger of slippage.

The brace body of the cervical brace in accord with the invention, is made from an upper and lower segment, which are separated from one another by a weakened zone. The upper segment is seated in the neck area in the manner of a conventional cervical brace, while the lower segment tightly encompasses the entire neck complex. This lower segment, which so encompasses the entire neck complex, prevents a slipping of the cervical brace in a circular direction, so that these cervical braces can be worn by the patients even in the night.

Without encroaching upon the wearing comfort, the lower segment enhances a greater degree of limitation of the movement possibilities of the spinal column in the neck and keeps the musculature warm. This gives rise to a better muscle relaxation then is the case with conventional cervical braces.

The brace body possesses, at least over a part of its length, a profile which connects it to the lower rim. Although that portion of the brace body, which encircles the neck area, that is, the upper segment, is relatively stable as to shape, that portion of the brace body which encircles the neck complex, that is, the lower segment, possesses greater flexibility, so that this part fits more closely about said neck complex.

From the standpoint of an optimum shape for fitting, the weakened zone advantageously does follow the lower circumferential contour of the brace element.

Advantageously, a groove, provided in the brace body, comprises the weakened zone. Because of the lessened material thickness of the brace body because of the groove a sufficient flexibility in the transition zone between the upper and lower segments is achieved. Instead of a groove, material strips can be inlaid, which provide a higher degree of flexibility.

In a preferred embodiment, the groove is provided on the outside of the brace body, wherein, this groove exhibits, an upper side running at an essentially right angle to the surface of the brace body and a lower side running at an angle thereto. The advantage of this embodiment is, that the upper side of the groove forms a detent for the lower segment of the brace body. The angle between the sides of the groove can be so dimensioned, that at a particular degree of slant to the lower segment in the area of the weakened zone, the brace body again achieves a measure of rigidity.

The brace body is advantageously comprised of elastic foamed rubber, which yet retains sufficient stability of shape. This said brace body, in case of necessity, can have a casing of skin-friendly textile material. Advantageously, the brace body is of one piece foam and is fashioned to be round in shape.

The cervical brace can also, of course, be designed as a flat body, which is wrapped around the neck of a patient. It can be made available in various sizes in order to find a well fitting shape.

BRIEF DESCRIPTION OF THE DRAWINGS

In the following, an embodiment of the invention will be more closely described, with the aid of the drawings.

There is shown in.

DETAILED DESCRIPTION

Figure 1:
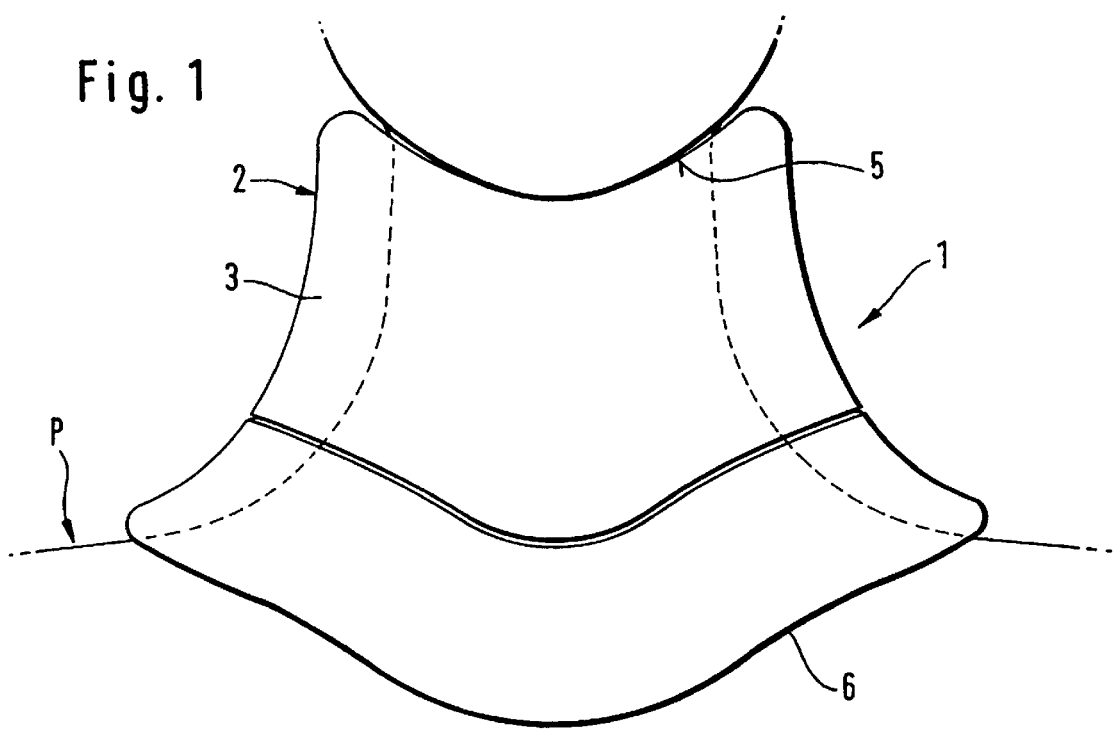
FIG. 1 a preferred embodiment of the cervical brace on the neck of a patient as seen from the front, FIG. 2 the cervical brace of FIG. 1 as seen from the side, FIG. 3 the cervical brace of FIG. 1 as seen from the back side, FIG. 4 the brace body of the flatly extended cervical brace of FIG. 1 in a view from above, FIG. 5 the brace body of the flat outspread cervical brace of FIG. 1 in a view from below, FIG. 6 a view in the direction of the arrow VI of FIG. 4, FIG. 7 a section along the lines VII—VII of FIG. 4 and FIG. 8 a section along the lines VIII—VIII of FIG. 4.
Figure 3:
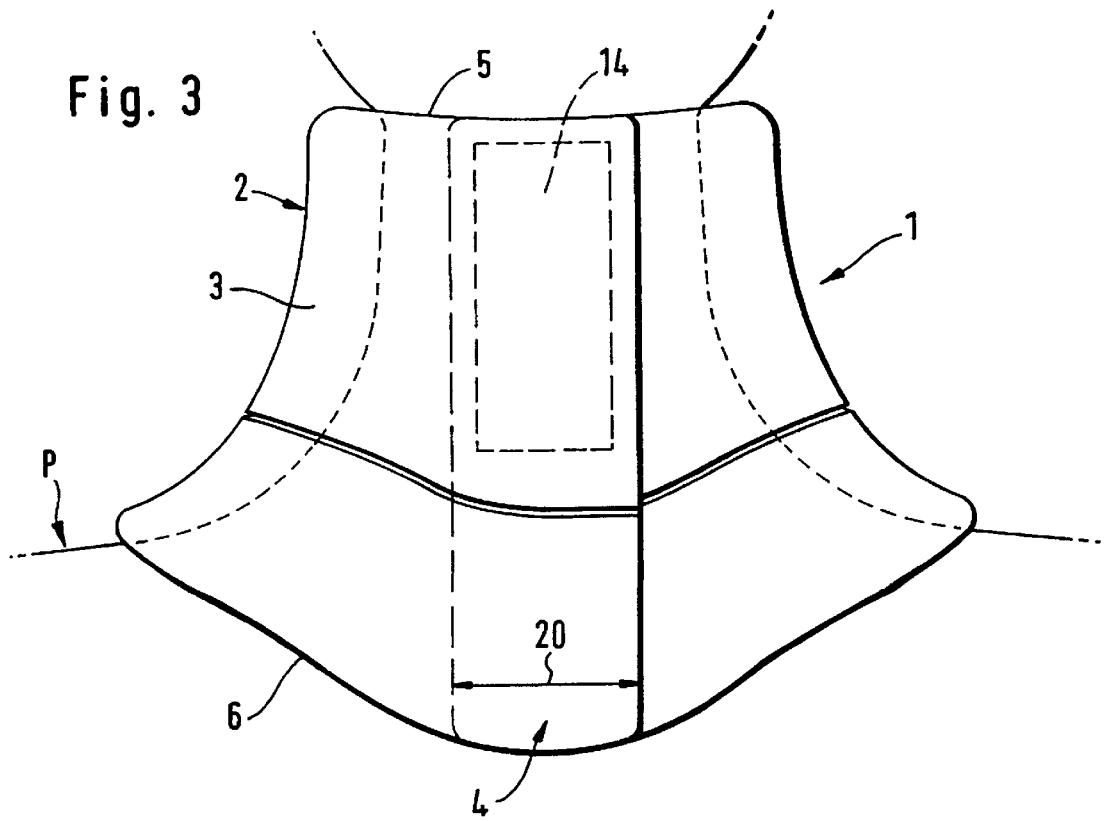
Figure 4:
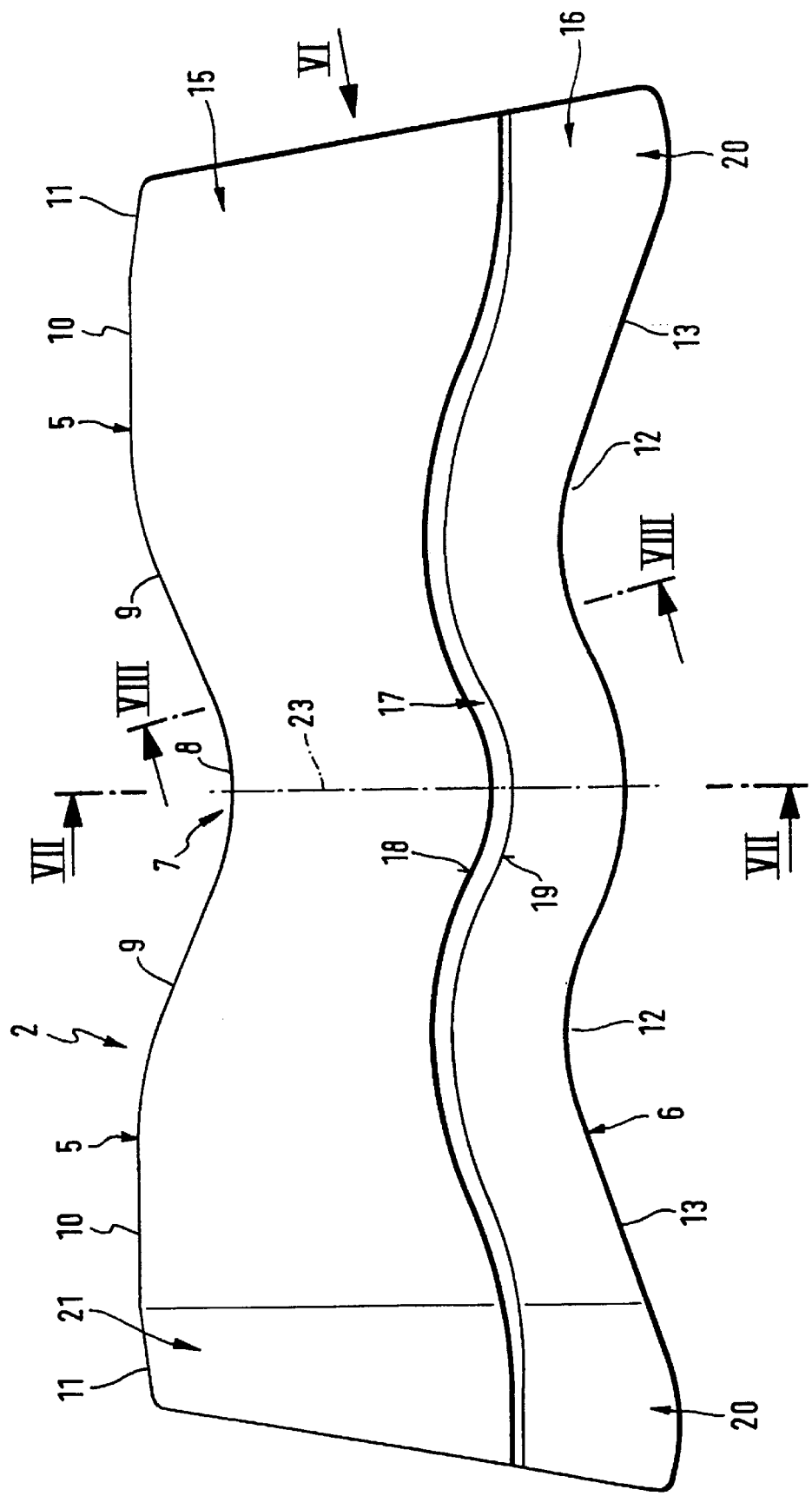
Figure 5:
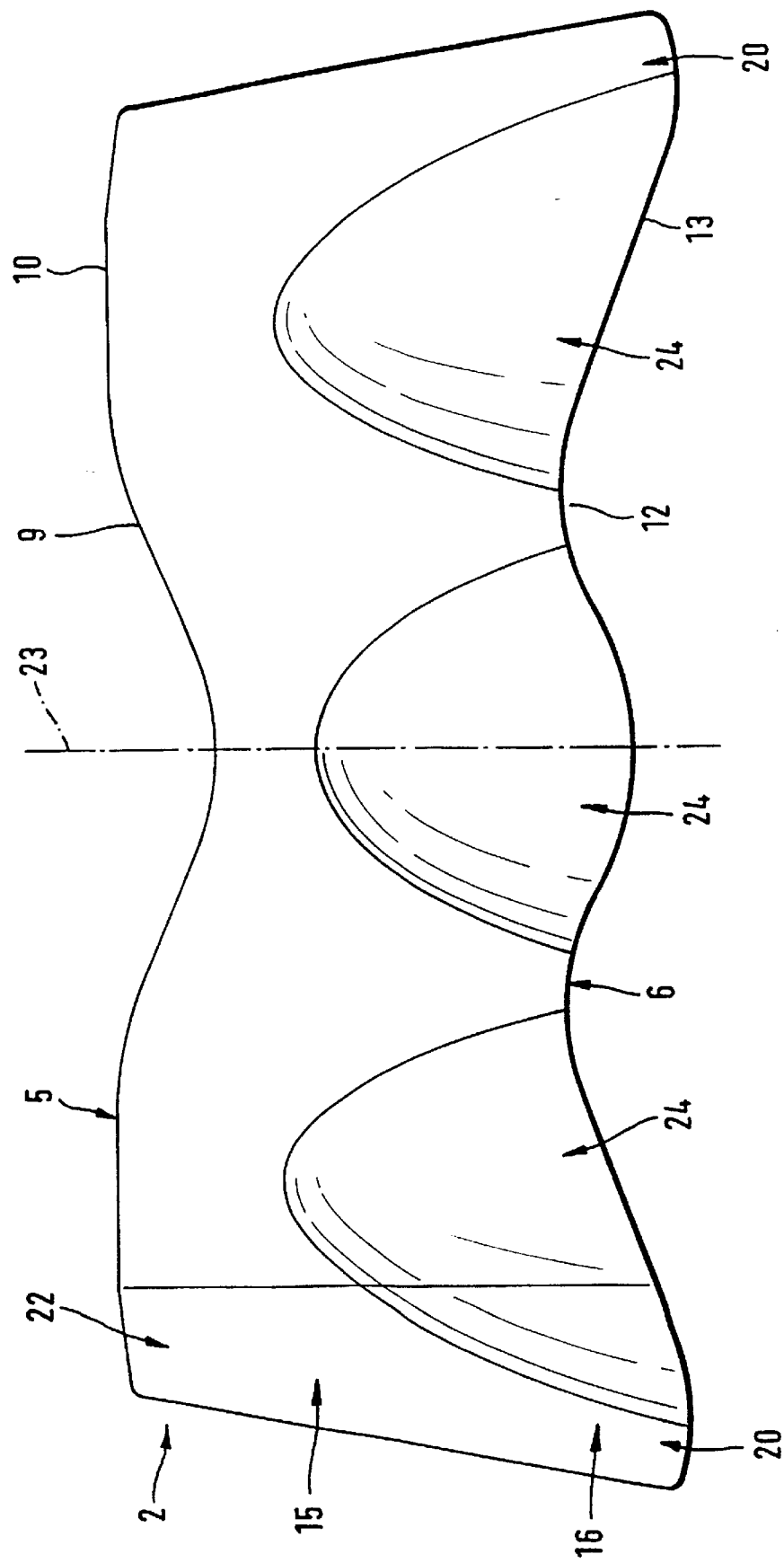

FIGS. 1 to 3 show the cervical brace 1 about the neck of a Patient "P", which cervical brace is essentially comprised of a flexible foam material of sufficiently shape retentive characteristics and covered with a skin-friendly, textile casing 3. The foamed material with a density of advantageously 40 kg/m² forms a body, which, because of its flexibility, can be spread out extensively. FIG. 4 shows in plan view, the brace body 2 of the cervical brace 1 which is spread out flat, that is the outside of the said brace body 2, while the inside of the brace body 2 is presented in FIG. 5.

The brace body fits the anatomy of the head and shoulder areas, where they border on the neck of the patient. At its upper rim 5, the brace body, in the area of the chin 7 is lightly cut away. This cutout 8 curves to each side as a curved brace 9, fitting the lower jaw. The brace 9 follows an essentially high level contour at 10, and then joins the ends by a slowly retrograding curve 11.

The brace body 2 on its lower rim 6 is cut away in a recess on both sides of the centerline. The cutouts 12 run steeply downward, following curve 13, and run on essentially to the ends of the brace body eventually overlapping themselves in the back of the neck of the patient. For fastening, on the ends of the brace body, hook and loop type closures 14 for example VELCRO® fasteners, are provided, which may be sewed on to the textile casing 3 (FIG. 3)

The brace body 2 possesses an upper and a lower segment 15, 16. The upper segment 15 is separated from the lower segment 16 by a longitudinal running groove 17 on the outer side of brace body 2. The course of the groove 17, with the exception of the area at the back of the neck 14, follows the contour of the lower rim 6 of the brace body 2. In the back of the neck area 14, the groove 17 runs on both sides of the brace body 2 essentially straight. The groove 17 possesses an upper side 18 running at right angles to the surface of the brace body 2 and a lower side 19 running at an angle thereto. The depth of the groove 17, i.e. to the bottom of the said groove, in the brace body 2 is essentially the same as the thickness of the material. The lower segment 16 has a breadth, which represents 20 to 40%, preferably 30% of the breadth of the combined brace.

The brace body 2 possesses in the overlapping area, on the outside of the one end and on the inside of the other end a tapered form 21, 22. Otherwise, the profiling of the brace body relative to the centerline, which has been provided with the reference number 23, is symmetric, so that in the following, only the profiling of the right side, as shown in Fig.4, will be described with the help of FIGS. 5–7. The outside of the brace body 2, except for the overlapping zone 20, is flat. The inside, on the other hand, is so profiled, that the brace body 2 fits tightly in and firmly encircles the neck area and lower neck area of the patient (FIGS. 1–3).

In the area of the chin zone 7, the brace body 2 possesses the greatest material thickness while the profile to the lower rim area tapers off. At both sides of the chin 7, the flat, trough like recesses 24 are inserted, which extend themselves to the overlapping area and are so designed, that the brace body is tapered in its approach to the lower rim. (See FIGS. 6 and 7.)

Along the lower rim contour 6 and along the upper rim contour 5, with the exception of the overlap 20, the brace body exhibits essentially the same thickness of material, whereby the material thickness of the lower rim, as compared to that of the upper rim, represents some 20 to 40%, preferably 30%.

The lower-segment, which provides support in the neck complex, prevents the cervical brace 1 from rotating circumferentially about the neck and increases the restriction of movement of the neck portion of the spinal cord, whereby an increase in muscle relaxation is derived without diminishing the measure of comfort. This effect is further enhanced by the inner contouring of the brace body to an anatomical fit.

Claimed is:

1. A cervical brace which can be applied to a neck of a patient, and which brace possesses a brace body, an upper rim and a lower rim of said brace body fit head and shoulder anatomy, respectfully, wherein said brace body is comprised of an upper segment and a lower segment, which segments are connected by a flexible weakened zone which extends for substantially a full length of the brace body, and wherein the brace body exhibits, at least over a portion of its length, a tapering curvature to its lower rim, so that the lower segment, upon application of the cervical brace, fits tightly around a neck complex.

2. A cervical brace in accordance with claim 1, wherein the weakened zone has a contour that essentially follows that of the lower rim of the brace body.

3. A cervical brace in accordance with claim 2, wherein the weakened zone in the brace body includes a groove.

4. A cervical brace in accordance with claim 3, wherein the groove is provided on an outside of the brace body, and wherein said groove has a continuous upper side at right angles to a surface of the brace body and a continuous lower side disposed at an angle to said upper side.

5. A cervical brace in accordance with one of the claims 1 to 4, wherein the brace body has material of the same thickness along the upper rim.

6. A cervical brace in accordance with claim 5, wherein the brace body is comprised of an elastic foamed material.

7. A cervical brace in accordance with claim 6, wherein the elastic foamed material is provided with a cover of a textile material.

8. A cervical brace in accordance with one of the claims 1 to 4, wherein the brace body is comprised of an elastic foamed material.

9. A cervical brace in accordance with claim 8, wherein the elastic foamed material is provided with a cover of a textile material.

10. The cervical brace of claim 1 wherein said upper segment and said lower segment are connected by an integral flexible weakened zone.

11. The cervical brace of claim 1 wherein said flexible weakened zone is continuous for the full length of said brace body.

* * * * *

UNITED STATES PATENT AND TRADEMARK OFFICE
CERTIFICATE OF CORRECTION

PATENT NO. : 6,165,146
DATED : December 26, 2000
INVENTOR(S) : Wolfgang Giebeler It is certified that error appears in the above-identified patent and that said Letters Patent is hereby corrected as shown below:

Column 1,
Line 11, delete "which is within the generic concepts of".
Line 12, delete "claim 1".

Signed and Sealed this

Thirtieth Day of April, 2002

Attest:

Attesting Officer

JAMES E. ROGAN
Director of the United States Patent and Trademark Office